United States Patent [19]

Bacolot

[11] Patent Number: 5,459,898
[45] Date of Patent: Oct. 24, 1995

[54] TOOTHBRUSH FOR PARTIAL DENTURE PLATE AND NATURAL TEETH

[76] Inventor: Leonard B. Bacolot, 500 N. Western Ave., Santa Maria, Calif. 93454

[21] Appl. No.: 329,636

[22] Filed: Oct. 26, 1994

[51] Int. Cl.⁶ .............................. A46B 9/04; A61C 15/00
[52] U.S. Cl. .................. 15/106; 15/167.1; 15/DIG. 5; 15/195; D4/133; D4/105
[58] Field of Search ................ 15/167.1, 167.2, 15/106, 190, 191.1, 167.3, 159.1, 160, 195, DIG. 5, 110; D4/133, 134, 130, 105, 111, 112, 104, 119, 128, 106; 132/309

[56] References Cited

U.S. PATENT DOCUMENTS

| 860,435 | 7/1907 | Bangs | 15/167.1 |
|---|---|---|---|
| 1,805,587 | 5/1931 | Manley | 15/167.1 |
| 1,813,076 | 7/1931 | Newell | 15/167.1 |
| 2,798,241 | 7/1957 | Cohen | 132/309 |
| 2,888,008 | 9/1959 | Rosenthal | 132/309 |
| 3,792,504 | 2/1974 | Smith | 15/167.1 |
| 4,610,045 | 9/1986 | Rauch | 15/167.1 |
| 4,911,187 | 3/1990 | Castillo | 15/167.1 |

FOREIGN PATENT DOCUMENTS

| 180491 | 1/1907 | Germany | 15/167.1 |
|---|---|---|---|

*Primary Examiner*—Gary K. Graham

[57] ABSTRACT

A toothbrush for partial denture plate and natural teeth wherein an elongate handle includes a brush head plate having a first matrix of bristles, with the first matrix of bristles including an arcuate profile to permit cleansing of natural teeth and partial plates, with a conical second matrix of bristles integral with the handle at a second end of the handle spaced from the first matrix of bristles, such that the conical second matrix of bristles is arranged for cleaning clasp openings within the partial denture plates, that in turn are secured to a user's natural teeth.

5 Claims, 3 Drawing Sheets

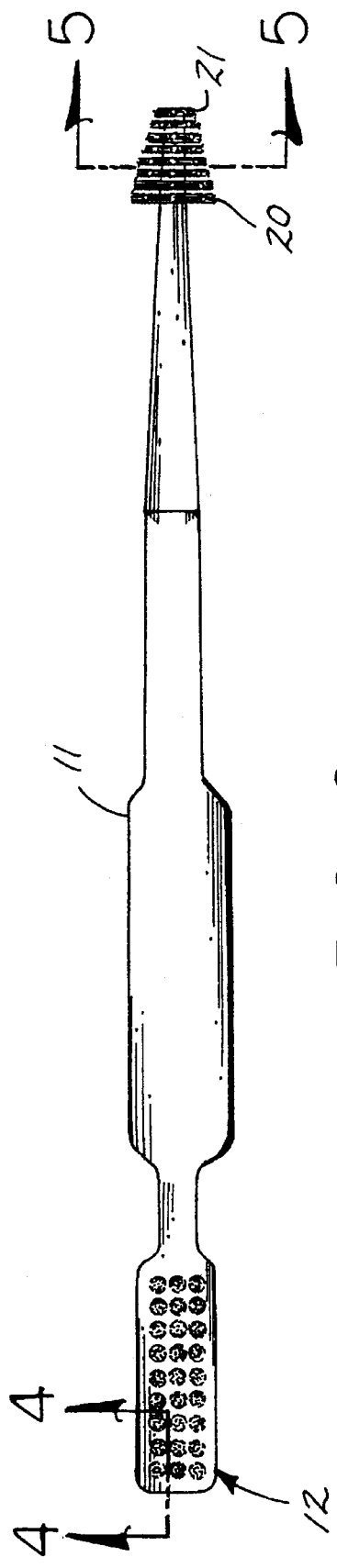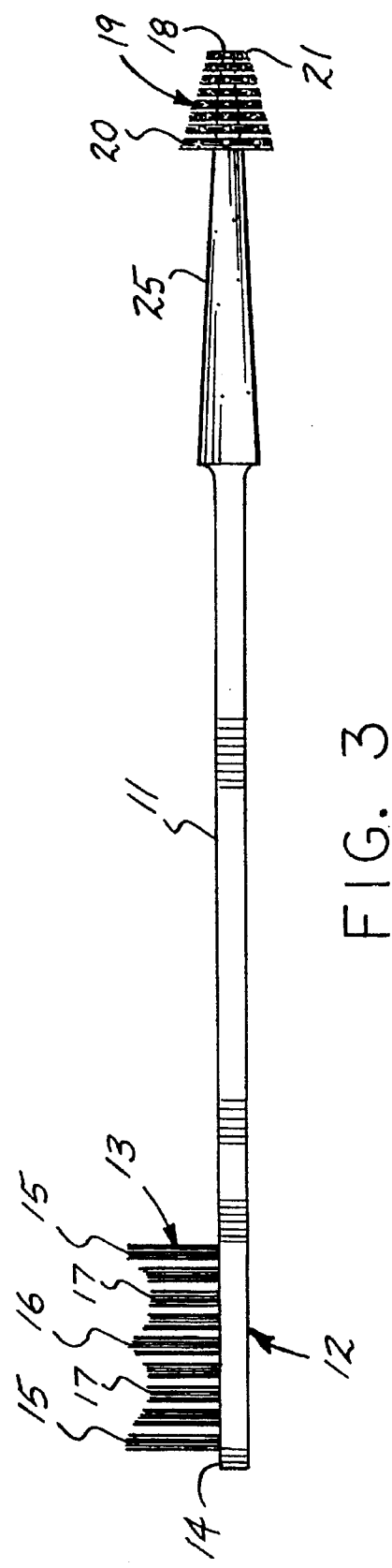

TOOTHBRUSH FOR PARTIAL DENTURE PLATE AND NATURAL TEETH

TECHNICAL FIELD

The field of invention relates to toothbrushing structures, and more particularly pertains to a new and improved toothbrush for partial denture plate and natural teeth wherein the same is arranged to permit effective cleaning of natural teeth and a partial denture plate in cooperation with such natural teeth.

BACKGROUND OF THE INVENTION

Prior art structure is available for addressing the cleaning of natural teeth and dentures as indicated in U.S. Pat. No. 4,888,844 utilizing a bulbous brush member head mounted to an end portion of an elongate handle. Other various toothbrushing structures are indicated and exemplified by the U.S. Pat. Nos. 5,228,466; 4,449,266; 5,100,252; and 4,048,690 wherein such various patents are arranged to address various concerns in a toothbrushing event.

SUMMARY OF THE INVENTION

To obtain this, the toothbrush for partial dentures and natural teeth as indicated by the instant invention employs an elongate handle, wherein a first end of the handle includes a brush head plate, wherein a first matrix of bristles includes an arcuate profile, wherein the arcuate profile is spaced from a top plate portion of the brush head plate for effective cleaning of various portions of the dental plate and natural teeth. The second end portion of the handle is configured as a conical handle portion, wherein the conical handle portion includes a truncated conical array of a second matrix of bristles extending from the second end of the handle structure to permit the cleaning of various openings and the like within partial denture plates that are typically arranged to engage the natural teeth.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an orthographic top view of the invention.

FIG. 3 is an orthographic side view of the invention.

DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
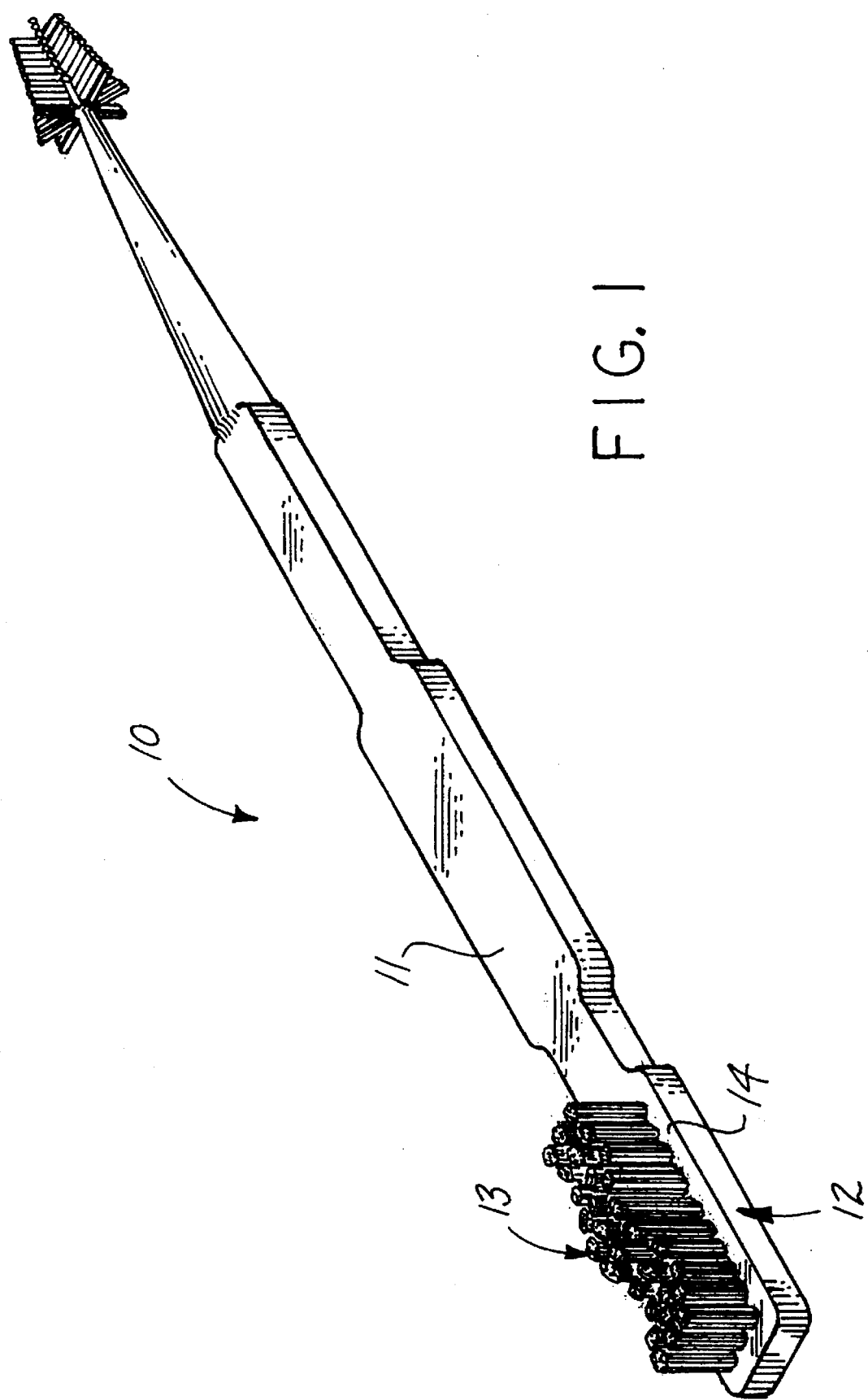
FIG. 1 is an isometric illustration of the invention.
Figure 5:
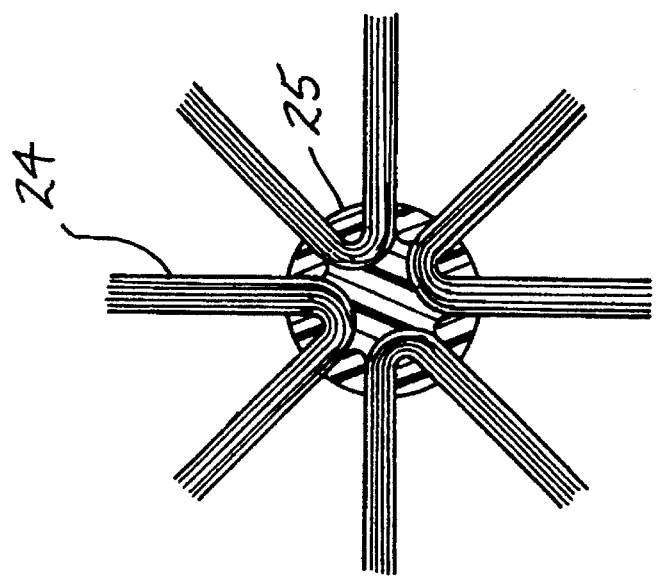
FIG. 5 is an enlarged orthographic view, taken along the lines 5—5 of FIG. 2 in the direction indicated by the arrows.
Figure 4:
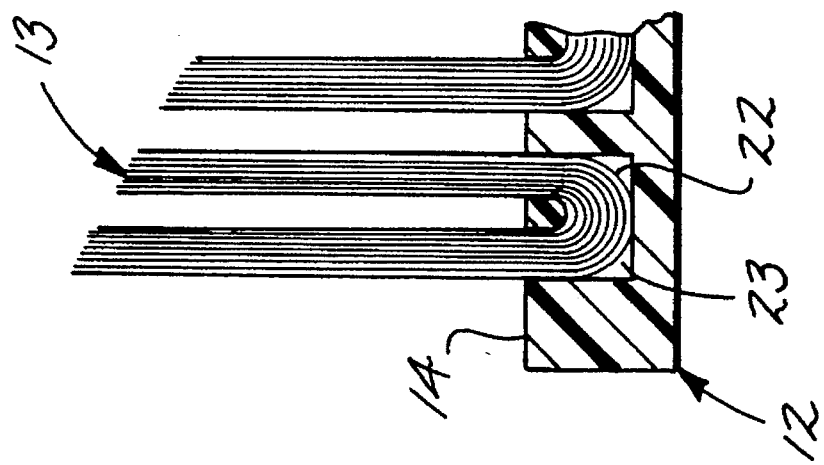
FIG. 4 is an enlarged orthographic view, taken along the lines 4—4 of FIG. 2 in the direction indicated by the arrows.

The toothbrush 10 of the invention employs an elongate handle 11, with a brush head plate 12 fixedly positioned at a first end of the handle 11, such that the brush head plate 12 is formed with a top wall 14 from which a first matrix of bristles 13 extends. The first matrix of bristles define an arcuate profile (see FIG. 3), wherein that profile is spaced from the top wall 14, and the first matrix of bristles 13 is formed of parallel rows of individual tufts of individual fibers 24 (see FIG. 4), wherein adjacent rows of the parallel rows of the tufts are of generally first U-shaped tufts of fibers 22, wherein the fibers of an individual tuft of one row is of a varying length of a tuft of fibers of a second row that protect from the top wall 14. The first matrix of bristles 13 are formed of the parallel rows such that outermost bristles 15 are of a first length typically and substantially one-half inch in length as measured from the top wall 14, wherein the central bristles 16 are also substantially of the first length, wherein the shortest bristles 17 of tufts of rows are medially of the central bristles 16 and the outer bristles 15 are configured of a second length substantially equal to three-eighths of an inch, and wherein the arcuate profile, as illustrated in FIG. 3, is configured such that the brushing of denture flanges and the inside area of dentures above the center incisors is made most effective in utilization of the instant invention. The handle 11 is formed with a generally conical handle portion 25 that extends from the central handle 11 to the handle second end 18, wherein a truncated conical configuration of a second matrix of bristles 19 is configured extending from the second end 18. The innermost bristles 20 define a first annular array 20 of the first length, with the outermost bristles defining a second annular array 21 at the second end 18 of a third length that are less than the second length that of course is less than the first length, wherein the third length is typically of one-fourth inch in length. Reference to the FIG. 5 indicates that the second matrix of bristles 19 of the row of bristles are also formed of annular arrays of tufts of bristles extending from the conical handle portion 25. The conical handle portion permits ease of configuring the second matrix of bristles 19. To this end, second U-shaped tufts of fibers 24 whose apex is imbedded within the conical handle portion 25 extend therefrom. It should also be understood, as illustrated in the FIG. 4, that the apex of the first U-shaped tufts of fibers 22 are each received within a head plate cavity 23 secured therewithin and in this manner, providing greater structural integrity to the tufts of bristles and the resultant rows that extend from the handle 11, and more specifically the head plate 12 and the conical handle portion 25 respectively. The truncated conical configuration defining the second matrix of bristles 19 are thusly arranged to permit the cleaning of holes in partial denture clasps that are employed to attach the partial denture plate to a user's natural teeth prior to their securement to the natural teeth thusly permitting the use of cleansers. The brush structure as such employing bristles of a more efficient configuration minimize need for harsh cleansing chemicals in cleaning of partial dentures.

It is to be understood that while certain forms of the present invention have been illustrated and described herein, it is not to be limited to the specific forms or arrangement of parts described and shown.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed and desired to be protected by Letters Patent of the United States is as follows:

1. A toothbrush, comprising, an elongate central handle, the handle having a handle first end, with a brush head plate integrally attached to the handle first end, and a generally conical handle portion extending from the central handle terminating in a handle second end, and the brush head plate having a brush head plate top wall, with the brush head plate top wall including a plurality of parallel rows of first bristle tufts defining a first matrix of bristles extending therefrom, the first matrix of bristles terminates in an arcuate profile with the arcuate profile spaced from the brush head plate top wall at the outermost distal end of the first matrix of bristles;

a conical second matrix of bristles integrally attached with and extending radially from the conical handle portion, said second matrix extends along the conical handle portion to the second end and is defined by a plurality of parallel annular rows of bristles.

2. A toothbrush as set forth in claim 1 wherein the first matrix of bristles has a pair of outer rows of bristles of a first length and a central row of bristles of said first length located between said outer rows, with shortest bristles positioned between the central row of bristles and each of the outer rows of bristles, wherein the shortest bristles are of a second length less than the first length.

3. A toothbrush as set forth in claim 1 wherein the first matrix of bristles include a plurality of first U-shaped bristles, wherein the first U-shaped bristles extend within adjacent rows of said parallel rows of the first matrix of bristles.

4. A toothbrush as set forth in claim 3 wherein each annular row of bristles of the second matrix of bristles includes U-shaped fibers, wherein an apex of said U-shaped fibers is imbedded within the conical handle portion.

5. A toothbrush as set forth in claim 1 wherein the conical second matrix of bristles is truncated.

\* \* \* \* \*